United States Patent

Kocache et al.

Patent Number: 5,324,951
Date of Patent: Jun. 28, 1994

[54] INFRA-RED SOURCE

[75] Inventors: Riad M. A. Kocache; Danny F. Holman, both of Crowborough; James Swan, Eastbourne, all of England

[73] Assignee: Servomex (UK) Ltd., Sussex, England

[21] Appl. No.: 30,223

[22] PCT Filed: Sep. 12, 1991

[86] PCT No.: PCT/GB91/01558
§ 371 Date: Mar. 16, 1993
§ 102(e) Date: Mar. 16, 1993

[87] PCT Pub. No.: WO92/05411
PCT Pub. Date: Apr. 2, 1992

[30] Foreign Application Priority Data

Sep. 18, 1990 [GB] United Kingdom ............... 9020388

[51] Int. Cl.$^5$ ............................................. G01J 1/00
[52] U.S. Cl. ............................ 250/493.1; 250/504 R
[58] Field of Search ............ 250/493.1, 495.1, 504 R; 273/348.1

[56] References Cited

U.S. PATENT DOCUMENTS

| 4,378,489 | 3/1983 | Chabinsky et al. | 250/493.1 |
| 4,620,104 | 10/1986 | Nordal et al. | 250/493.1 |
| 4,859,858 | 8/1989 | Knodle et al. | 250/493.1 |
| 4,883,971 | 11/1989 | Jensen | 250/493.1 |
| 4,922,108 | 5/1990 | Modlinski et al. | 250/495.1 |
| 5,220,173 | 6/1993 | Konstad | 250/493.1 |

FOREIGN PATENT DOCUMENTS 917160  1/1963  United Kingdom .

Primary Examiner—Bruce C. Anderson
Attorney, Agent, or Firm—Cumpston & Shaw

[57] ABSTRACT

A miniature source of modulated infra-red energy comprises a very thin heated wire strip (11) of low mass, mounted in a tensioned state by means of two resilient members (18), and a reflector (15) positioned behind the wire (11) so as to enhance the radiated energy. The source is hermetically sealed in an inert atmosphere with a cap (20). The cap (20) has an aperture (16) through which the energy emerges, this is sealed either with a window or a filter (17) if a specific wavelength is desired.

9 Claims, 3 Drawing Sheets

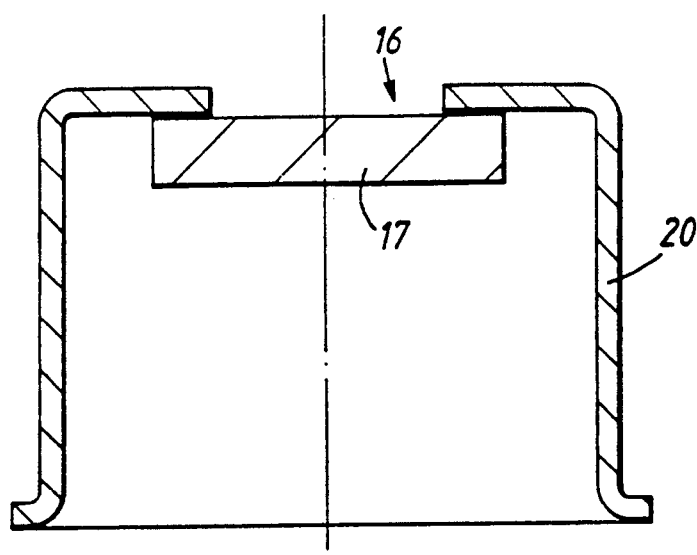
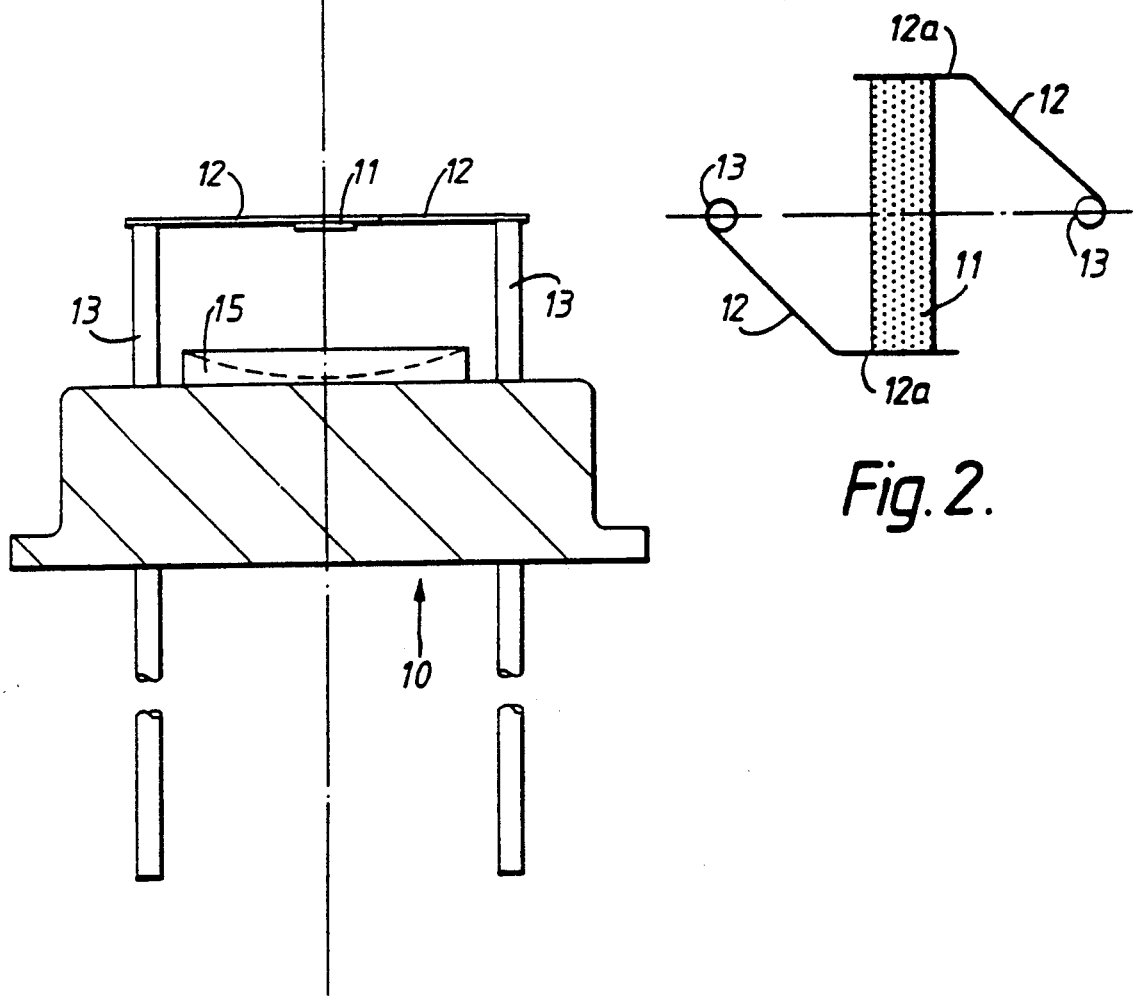
Fig. 2.
Fig. 1.

INFRA-RED SOURCE

This invention relates to an infra-red source particularly for use in a non-dispersive type of infra-red analyser.

The simplest form of such an analyser (a single beam, single waveform photometer) would normally consist of: an infra-red source, a beam modulator, a sample cell, a photo detector system, and an electronic system. In a gas analysis system, the cell is initially filled with a gas such as air which does not absorb infra-red and the system is zeroed. A calibration gas of known composition, the same as the gas to be monitored and which absorbs infra-red, is used to calibrate the instrument.

The infra-red source could be a Nernst element, a glow-bar or simply a heated wire which radiates in the infra-red region. The infra-red beam is usually modulated by mechanical means such as a chopper motor, an actuator or a tuning fork. The beam is allowed to pass or is stopped periodically by such means. An IR filter is sometimes placed on the chopper so that the beam passes through a filter selected in relation to the substance to be analysed. The modulated beam goes through the sample cell and then impinges on the photo detector which with the help of an electronic system gives a signal which is displayed.

The main reasons for modulating the infra-red beam are to be able to process the signal in an AC mode, and the need to handle transient signals such as breath-by-breath analysis of exhaled gases requiring a speed of response of the analyser in the region of 100 milliseconds.

Experience has shown mechanical choppers to be bulky and unreliable. This made some designers use small filament lamps and operate them in a switched mode, dispensing with a mechanical modulator. These however have the disadvantage of being enclosed in an ordinary glass envelope which absorbs infra-red energy. They also suffer from an uncertain life time and drift due to the movement of the filament when heated.

There are sources now available based on thin film technology and ones on semi-conductor technology which can be modulated. These however are costly.

Thus there is a need for a relatively low power low cost infra-red source which avoids the problems of mechanical beam modulators and which minimises the problems of thermal drift, short-lifetime and cost.

The present invention provides an infra-red source comprising a support base, a strip of material capable of radiating infra-red emissions, means arranged to allow connection of said strip across a source of electrical power, and two resilient mounting members provided on said support base each attached adjacent a respective end of said strip and arranged to support said strip in a tensioned state.

There is therefore provided an infra-red source which is capable of being operated in a switched mode at a frequency in the region 0.5-30 Hz. Typically the source according to this invention operates at a relatively low temperature, i.e. below 1050K.

For infra-red spectrophotometry, it is important that the infra-red source be stable both in radiation intensity and in physical position so as to reduce the drift in the apparatus to a minimum. The strip of material providing the infra-red emission in this invention is symmetrically resiliently mounted. This causes the centre of the strip to remain stationary even when the strip expands due to the increase in temperature during operation, and also maintains the tensioning of the strip.

In the source according to this invention electrical connection to the strip may be by way either of the resilient mounting members themselves or by means separate from the resilient mounting members. The source of the invention is typically low power, e.g. 1 W, and is generally of a small physical size.

In GB 917160 there is disclosed a means for supporting a tungsten filament in a high-intensity incandescent-filament source, that is to say a source of light or heat in which the filament is required to operate at temperatures exceeding 2500 K. In such a source, which generally operates continuously, a sagging filament leads to a very short life. Thus GB 917160 provides means for resiliently mounting the filament in order to improve the operating life. The arrangement of GB 917160 is not specifically useful for low power sources, such as described by the present invention, "since with sources of lower power, and consequently having smaller filaments, the difficulty of fabricating the clamps, and the added heat loss due to thermal conduction along them may outweigh the advantage derived from the use of the invention". (page 1 line 79 to page 2 line 5).

In order that the present invention be more readily understood an embodiment thereof will now be described by way of example with reference to the accompanying drawings, in which:

FIG. 1 is an exploded, sectional side view of an infra-red source according to the present invention;

FIG. 2 is a plan view illustrating the mounting of the strip in the source showning FIG. 1.

The preferred form of infra-red source according to the invention and illustrated in FIG. 1 is similar in many respects to a transistor can in as much as it is formed of a support base 10 provided with terminals and covered by a cap 20 to provide a hermetically sealed space.

Figure 3:
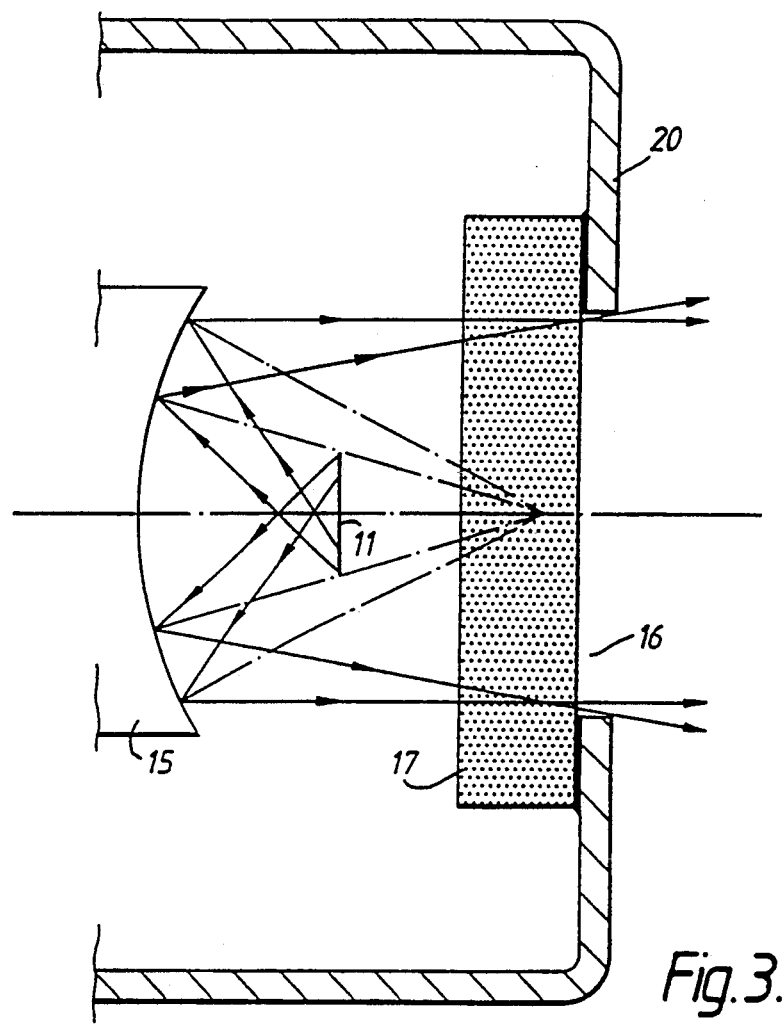
FIG. 3 is a diagrammatic sectional side view of the source shown in FIG. 1.

Within the space formed by the support base 10 and cap 20, a thin uniform strip 11 of a material that radiates infra-red energy efficiently such as 80/20 nichrome is tautly and evenly suspended between two resilient supports 12. The supports 12 should be of adequate strength so as to apply to the strip 11 a force of at least 15% of its breaking force. The supports 12 are made of wire which is bent into a shape which allows the strip to be stretched between the two parallel arms 12a of the supports 12 and place it in a plane parallel to an aperture 16 in the cap 20. The ends of the springs are welded to the electrical pins 13 of a standard transistor type support base or header 10. The strip 11 is also joined by welding to the supports 12. The springs are normally set in an unparallel position before the welding and brought into the parallel position during the welding process, this ensures that the strip 11 is under tension and minimizes the mechanical movement of the strip during the heat up cycle, and in addition reduces the possibility of vibration induced movement. A typical size of the strip is 5 micron thick 0.75 mm wide and 4 mm long, for an aperture of 3 mm diameter; a typical resilient support is a 20/80 Pt/IR wire 0.20 mm diameter. A reflector 15 is cemented to the base of the header and enables the back radiated beam to be reflected and passed through aperture 16 together with the direct beam from strip 1. The curvature of the reflector is preferably a circle of a radius about the same size as the diameter of the aperture in the cap. This ensures an optimum collection of energy and is represented by the diagrammic view shown in FIG. 3.

When the strip is heated to the upper working temperature, e.g. 750° C., it elongates. The typical elongation in a 4 mm long strip is 0.04 mm. The tension in the supporting springs ensures that the slack caused by this elongation is taken up and the strip is not allowed to sag.

However, in the mounting arrangement of FIG. 2, because the shape of the springs 12 is straight, when the springs 12 move apart to take up the slack, parts 12a twist with respect to strip 11 causing a twist along the strip and a movement of the source. This may be acceptable when the source is working at lower temperatures e.g. 450°-550° C., but is unacceptable at higher temperatures.

Figure 4:
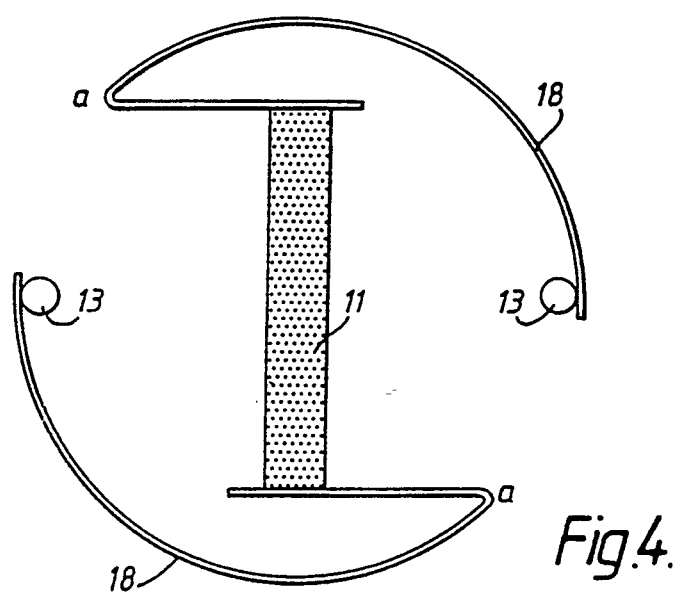
FIG. 4 is a plan view illustrating an alternative arrangement for mounting the strip to that illustrated in FIG. 2.

An alternative arrangement which reduces this problem is illustrated in FIG. 4. In this arrangement strip 11 is mounted on springs 18 which are welded to pins 13. This arrangement may be used in the source illustrated in FIG. 1 as a direct replacement for the arrangement of FIG. 2. Springs 18, which are formed of the same material as springs 12 in FIG. 2, are shaped to have a major portion in the form of an arc centered on the centre of strip 11 having a radius approximately equal to $\sqrt{2} \times 1$, where 1 is half the length of strip 11. One end of each spring 18 is welded to one of the pins 13. At the other end of each spring 18 is a straight portion which subtends an angle of 45° with the tangent to the arc at point 'a' as illustrated in FIG. 4. Strip 11 is welded to and held between the straight portions of springs 18.

Figure 5:
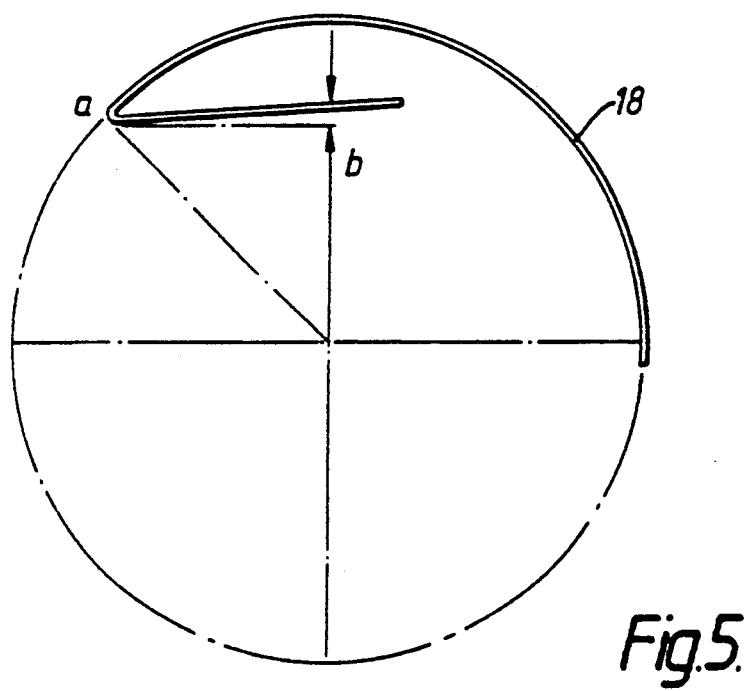
FIGS. 5 and 6 are diagrams useful to explain the mounting arrangement illustrated in FIG. 4.
Figure 6:
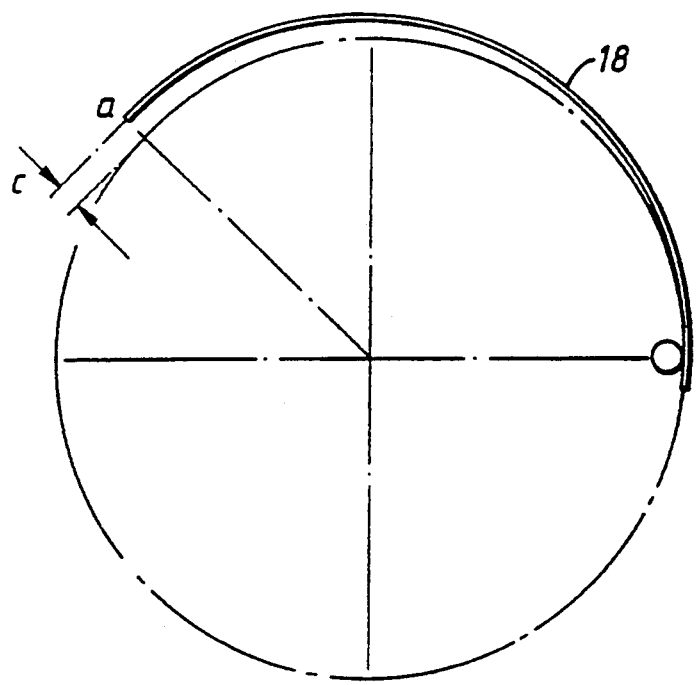

The shape of springs 18 described above is that taken up when they are in use. Springs 18 take a slightly different shape when they are not attached to strip 11, thus enabling them to apply the required tensioning force to strip 11 when they are deformed into the shape described above. The natural form of springs 18 is illustrated in FIGS. 5 and 6. The straight portion of spring 18 is bent such that it has a deflection 'b' at the centre of strip 11 from its position illustrated in FIG. 4 when the arcuate portion is in position. The arcuate portion of spring 18 is formed so as naturally to have a deflection 'c' at point 'a' from the position as illustrated in FIG. 4. For a strip with dimensions as described above, typical values of 'b' and 'c' are 0.05 mm and 0.10 mm respectively.

As illustrated in FIG. 4, the arcurate portions of springs 18 are brought into line with a circle having a radius $\sqrt{2} \times 1$ and the straight portions become horizontal (in the orientation of FIG. 4) when strip 11 is welded between the springs. The effect of this is that as the strip elongates the two springs acting on the strip act differentially and reduce the amount of twist in the strip to a minimum.

The aperture 16 is sealed by a window 17 which is cemented by use of epoxy adhesives, other cements or by metalising the window and brazing it to the cap. The window 17 can be a wide band infra-red transmitting medium such as sapphire, germanium, etc. or a filter chosen specifically to pass a chosen band of infra-red. The cap is joined to the base in an inert atmosphere (e.g. nitrogen) by resistance welding, argon arc welding, laser welding or brazing.

In a further modification, the heated strip 11 would be made of a material whose resistivity is a known function of temperature such as platinum. This would allow the source to be operated at a constant temperature when turned on by monitoring the resistance of the element, and turning the power off when the preselected temperature which corresponds to a prechosen temperature is reached.

We claim:

1. An infra-red source comprising a support base, a strip of material capable of radiating infra-red emissions, means arranged to allow connection of said strip across a source of electrical power, and two resilient mounting members provided on said support base each attached adjacent a respective end of said strip and arranged to support said strip in a tensioned state.

2. A source according to claim 1, and comprising a reflector disposed between the strip and the base.

3. A source according to claim 1, and comprising a cap arranged to be supported on the base and form a housing therewith, the cap being provided with an aperture to permit emission of infra-red radiation from the strip.

4. A source according to claim 3, wherein the aperture is provided with a material which is transmissive of a wide band of infra-red radiation.

5. A source according to claim 3, wherein the aperture is provided with a material which is transmissive of a selected narrow band of infra-red radiation.

6. A source according to claim 3 wherein the aperture in the cap is generally planar and the strip is a uniform planar strip of material mounted such that the plane of the strip is substantially parallel to the plane of the aperture.

7. A source according to claim 6, wherein the strip is of nichrome.

8. A source according to claim 1, wherein the strip is a uniform planar strip of material.

9. A source according to claim 1 wherein the tensioning force applied to the strip is at least 10% of the breaking force of the strip.

* * * * *